(12) United States Patent
Normand (10) Patent No.: US 8,411,267 B2
(45) Date of Patent: Apr. 2, 2013

(54) POLARIMETRIC HYPERSPECTRAL IMAGER

(75) Inventor: Erwan Normand, Stirling (GB)

(73) Assignee: Cascade Technologies Limited, Stirling (GB)

( * ) Notice: Subject to any disclaimer, the term of this patent is extended or adjusted under 35 U.S.C. 154(b) by 376 days.

(21) Appl. No.: 12/677,903

(22) PCT Filed: Sep. 1, 2008

(86) PCT No.: PCT/GB2008/002956
§ 371 (c)(1),
(2), (4) Date: May 14, 2010

(87) PCT Pub. No.: WO2009/034296
PCT Pub. Date: Mar. 19, 2009

(65) Prior Publication Data
US 2011/0170098 A1     Jul. 14, 2011

(30) Foreign Application Priority Data
Sep. 14, 2007   (GB) .................................. 0717967.4

(51) Int. Cl.
*G01J 3/00*   (2006.01)
(52) U.S. Cl. ........................................................ 356/300
(58) Field of Classification Search .................. 356/402, 356/300; 372/9
See application file for complete search history.

(56) References Cited

U.S. PATENT DOCUMENTS

| | | | | |
|---|---|---|---|---|
| 5,095,487 A | * | 3/1992 | Meyerhofer et al. | ........... 372/23 |
| 6,163,378 A | * | 12/2000 | Khoury | ........................ 356/457 |
| 2004/0202399 A1 | * | 10/2004 | Kochergin et al. | ............... 385/12 |
| 2005/0023470 A1 | * | 2/2005 | Ferguson et al. | .......... 250/358.1 |
| 2005/0111816 A1 | * | 5/2005 | Birk et al. | ..................... 385/147 |
| 2005/0157303 A1 | * | 7/2005 | Langford et al. | ............. 356/437 |

FOREIGN PATENT DOCUMENTS

| | | |
|---|---|---|
| JP | 2002539446 A | 11/2002 |
| JP | 2006145362 A | 6/2006 |
| JP | 8136455 A | 11/2006 |
| RU | 2288461 C2 | 11/2006 |
| WO | WO00/55602 | 9/2000 |
| WO | WO02/48687 A3 | 6/2002 |
| WO | WO03/087787 A1 | 10/2003 |
| WO | WO2005/115737 A2 | 12/2005 |

OTHER PUBLICATIONS

Normand et al., "Fast, real-time spectrometer based on a pulsed quantum-cascade laser", Jan. 1, 2003, Optics Letters, vol. 28, No. 1, pp. 16-18.*
M. J. Wabomba et al: "Remote Detection of Volatile Organic Compounds by Passive Multispectral Infrared Imaging Measurements" Applied Spectroscopy, 2007, vol. 61, No. 4, pp. 349-358.
I. Howieson et al.: "Quantum-cascade lasers smell success" Laser Focus World, Mar. 2005, vol. 41, No. 3, pp. 1-3.

(Continued)

*Primary Examiner* — Kara E Geisel
(74) *Attorney, Agent, or Firm* — Moore & Van Allen, PLLC; W. Kevin Ransom (57) ABSTRACT

A hyperspectral sensor or imager comprising a laser for illuminating a scene and a detector for detecting light emitted by the laser and transmitted through the scene, wherein the laser is a chirped laser arranged to output multiple pulses having different wavelength ranges, the multiple pulses being used to form an extended continuous spectrum for illuminating the scene.

29 Claims, 7 Drawing Sheets

OTHER PUBLICATIONS

M. T. McCulloch et al: "Highly sensitive detection of trace gases using the time-resolved frequency downchirp from pulsed quantum-cascade lasers" Journal of the Optical Society of America, Aug. 2003, vol. 20, No. 8, pp. 1761-1768.

R. Maulini et al.: "Broadband tuning of external cavity bound-to-continuum quantum-cascade lasers" Applied Physics Letters, Mar. 8, 2004, vol. 84, No. 10 pp. 1659-1661.

J. D. Berger et al.: "Tunable MEMS Devices for Optical Networks" Optics & Photonics News, Mar. 2003, vol. 14, No. 3, pp. 42-49.

M. J. Weida, et al., "Tunable QC laser opens up mid-IR sensing applications" Laser Focus World, Jul. 2006, pp. 1-2.

A. Lytkine et al: "Frequency chirped differential absorption LIDAR" Proc. of SPIE, Sep. 29, 2006, vol. 6367, p. 63670J-1-63670J-9.

International Search Report for PCT/GB2008/002956, dated Jul. 1, 2009.

Russian Office Action in RU Application No. 2010115021, received Sep. 11, 2012.

Howieson et al.: "Quantum-cascade lasers smell success"; Laser Focus World, Mar. 2005, vol. 41, No. 3, pp. 1-3.

Japanese Office Action issued in JP Application No. 2010-524561, dated Dec. 4, 2012.

* cited by examiner

Figure 1(a)
(prior art)

Type 1

Type 2

POLARIMETRIC HYPERSPECTRAL IMAGER

FIELD OF THE INVENTION

The present invention relates to a spectro polarimetric hyperspectral imager. In particular the invention relates to a hyperspectral imager that uses a quantum cascade laser.

BACKGROUND OF THE INVENTION

Figure 1A:
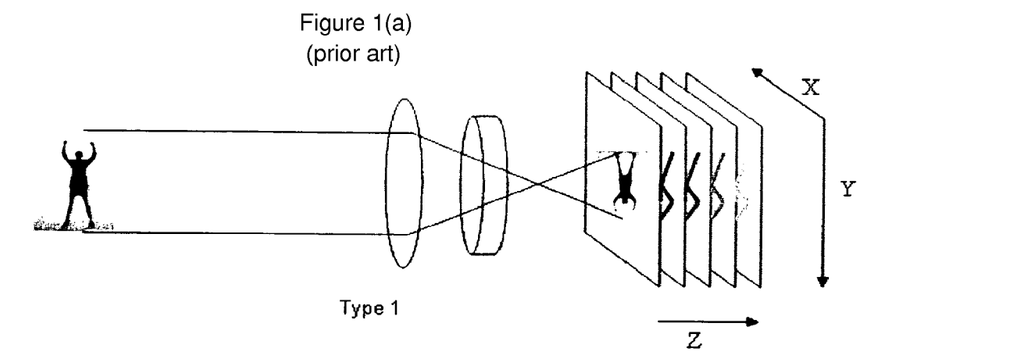
FIG. 1(a) is a depiction of a hyperspectral imager having a wavelength scanning system that measures an image slice at a fixed wavelength.
Figure 1B:
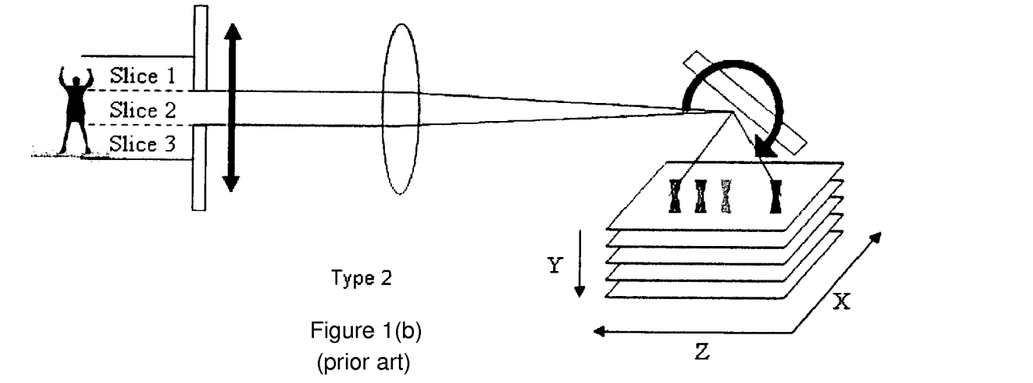
FIG. 1(b) is a depiction of a hyperspectral imager having a slit or line scanning systems that measures a spectral slice at a fixed position either by scanning spectrally by rotating diffractive optics or spatially by moving the line position through a slit.

Hyperspectral imaging is the imaging of a scene over a large number of discrete, contiguous spectral bands. There are two basic types of hyperspectral imager: wavelength scanning systems that measure an image slice at a fixed wavelength, as shown in FIG. 1(a) and slit or line scanning systems that measure a spectral slice at a fixed position either by scanning spectrally by rotating diffractive optics or spatially by moving the line position through a slit, as shown in FIG. 1(b). The dataset acquired by such imagers is generally referred to as a data cube, where the first two dimensions are given by the image of the scene area, that is the spatial information, and the third is given by the spectral information.

Hyperspectral sensors carry out imaging spectrometry to retrieve spectroscopic features. When a gas cloud is present between a hyperspectral sensor and the scene under observation, the cloud absorbs/emits light that produces a contrast with light reflected or naturally emitted by the scene at a particular wavelength. By scanning in wavelength while imaging the scene and then comparing the spectral information with and without the gas (i.e. carrying out a contrast analysis), the absorption/emission features of the gas can be obtained and used to identify the compound(s) within it. Hence, these sensors can give advance warning of hazardous chemical vapours undetectable by eye, as well as monitor the species concentrations in a gas. In the power plant sector, for example, some of the gas plumes that are of interest are CO, $CO_2$, $SO_2$, NO, $NO_2$. With a hyperspectral gas sensor, even low concentration vapour can be imaged, identified and measured.

Whilst hyperspectral imagers have the potential to be extremely powerful in the detection of hazardous materials, their use has been relatively limited. This is partly because many such imagers require moving parts, which limits their use in difficult environments, see M. J. WABOMBA et al., Applied Spectroscopy Volume 61, number 4, 2007. In addition, the wavelengths particularly suited to chemical fingerprinting of hazardous compounds such as illegal drugs, toxic industrial chemicals, explosive compounds, etc are generally in the Long Wave IR (LWIR) or thermal IR band, generally defined by the wavelength range covering 7 to 14 µm. Operating in the LWIR has significant drawbacks because the background scene stores energy from blackbody sources, e.g. the sun, and releases them via radiation at wavelengths corresponding to the LWIR band. In contrast in the short wave IR (SWIR) band, i.e. 1.5 to 3 µm wavelength range and the mid-wave IR (MWIR) band, i.e. the 3-5 µm range the scene tends to reflect incoming radiation. Hence, because the returned optical power density is more important in the SWIR and MWIR than the LWIR, therefore improving the signal to noise ratio relative to the background noise, many state of the art hyperspectral imager/sensor systems perform relatively well in the SWIR and MWIR bands, but not in the LWIR band.

SUMMARY OF THE INVENTION

According to the present invention, there is provide a hyperspectral sensor or imager comprising a laser for illuminating a scene and a detector for detecting light emitted by the laser and transmitted through the scene, wherein the laser is a chirped laser arranged to output multiple pulses having different wavelength ranges, the multiple pulses combining to form a continuous spectrum for illuminating the scene.

The continuous spectrum can be a narrow band spectrum, for example, a couple of wavenumbers, e.g. 2 $cm^{-1}$ (or 60 GHz expressed as a frequency), at the wavelengths of interest (narrowband mode). In this case, the laser may be a single mode chirped laser. By using the wavelength chirp of a single mode laser to provide a wavelength scan to actively image the scene, there is provided a very simple and effective scanning imaging system that does not require any moving parts. Compared with the conventional arrangements of FIG. 1, this provides improved reliability and robustness, thereby extending the system lifetime.

The continuous spectrum can be a broadband spectrum, for example, one hundred or so wavenumbers, e.g. 100 $cm^{-1}$ (or 3000 GHz expressed as a frequency) at the wavelengths of interest (broadband mode). In this case, the laser may be a multi longitudinal mode laser. By using the wavelength chirp of a multi longitudinal mode laser to provide a wavelength scan to actively image the scene, there is provided a very simple and effective method to emit broadband emission of coherent radiations with contiguous wavelength or nearly contiguous wavelength over a spectral range define by the overall gain spectrum of the laser. The multi longitudinal modes of the laser may be spectrally spaced by 60 to 240 GHz (i.e. two to eight wave numbers) to ensure emission contiguous wavelength over the all gain spectrum of the laser.

When coupled with a tunable spectral filter, the broadband spectrum sensor or imager can be used to form a scanning imaging system that does not require any moving parts. The tunable spectral filter may be a solid-state tunable spectral filter such as a liquid crystal fabry perot or acousto-optic tunable filter. Preferably, the filter is placed between the laser and the detector. Additionally or alternatively, a micro-electro-mechanical system based tunable filter may be directly integrated onto the detector array.

Alternatively or additionally, means for forcing the multi longitudinal mode laser to emit radiation in a single mode may be coupled onto the laser so that a tuning range of the single mode covering the overall gain spectrum of the laser is achieved, in order to form a scanning imaging system that does not require any moving parts.

The means for forcing the multi longitudinal mode laser to emit radiation in a single mode may comprise a micro-electro-mechanical system based spectral element, for example using the principle external cavity feedback (ECF). The micro-electro-mechanical element may be directly integrated onto the laser.

The laser may be a quantum cascade laser. Each pulse applied to the laser may have a duration that is greater than 50 ns, in particular greater than 100 ns. Each applied pulse may have a duration that is in the range of 50 to 3000 ns, preferably 100 to 3000 ns. This can provide a tuning range of about 60 to 240 GHz per pulse.

The different laser output pulses may be generated by varying one or more of the following features of the pulse applied to the laser: pulse width; pulse amplitude; pulse frequency.

The sensor/imager may include one or more polarization filters. The filters may be selected to suppress the LWIR background signal emitted by the scene. By allowing only specific polarized radiation to fall onto the detector array, for example the polarized components of the radiation emitted by the laser source, the LWIR background signal emitted by the scene can be efficiently suppressed, so that all that is observed are changes present in the active return signal due to a gas cloud located between the sensor and the background scene.

Additionally or alternatively, the detector may be polarization sensitive, for example the detector may be a quantum well infrared photo-detector. Preferably, the detector is operable to detect only polarized light generated by the chirped laser, which inherently a linearly polarized radiation source. This improves the signal to noise ratio of the return optical signal relative to the background noise, which is generally non-polarized.

The detector may be a two-dimensional focal plane detector. The detector may be a QWIP. The detector may be one of: a mercury cadmium telluride (MCT) detector; a selenide based detector; a superlattice type II detector.

BRIEF DESCRIPTION OF THE DRAWINGS

Various aspects of the invention will now be described by way of example only and with reference to the accompanying drawings, of which.

SPECIFIC DESCRIPTION OF THE DRAWINGS

Figure 2:
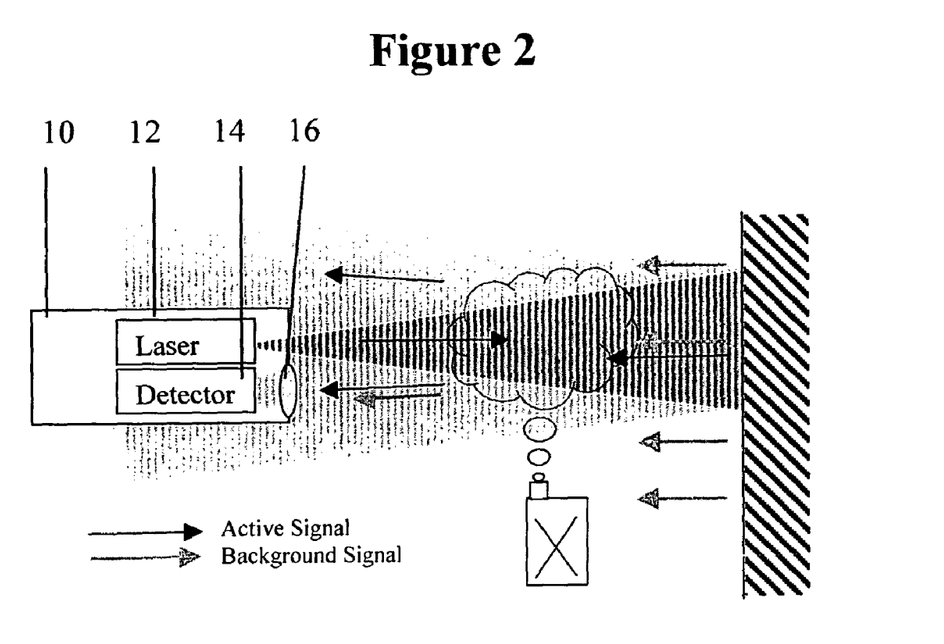
FIG. 2 is a block diagram of a hyperspectral sensor.

FIG. 2 shows a system 10 for acquiring both spectral and spatial information from an observed scene using a chirped laser hyperspectral imager. This includes a quantum cascade laser 12 for illuminating a scene, a detector 14 for detecting the laser light reflected from the scene and a lens 16 for focusing the reflected light onto the detector 14. Ideally, the detector 14 is a quantum well infrared photodetector. In use, the wavelength scan provided by each chirp output from the laser can be used to determine the presence or otherwise of a gas. This system has no moving parts, is inherently robust and can be made lightweight. Moreover, it offers enhanced performance in sensitivity and dynamic range.

Figure 3:
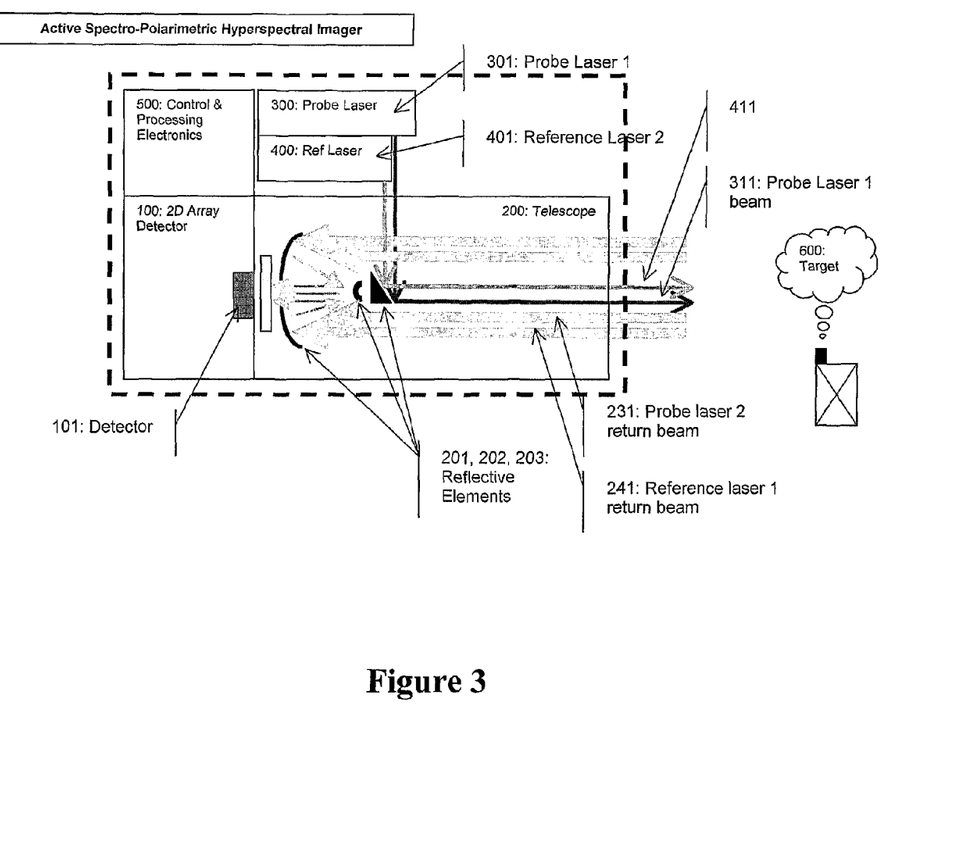
FIG. 3 is a more detailed view of the sensor of FIG. 2.

FIG. 3 shows a more detailed implementation of the imager 10 of FIG. 2. This has a quantum cascade probe laser 300 and a quantum cascade reference laser 400 for illuminating a scene of interest. To detect light reflected by the scene of interest, a 2D detector array 101 is provided. Control and processing electronics (not shown) are provided for controlling operation of the sensor/imager. The detector is a QWIP, incorporating a grating structure that selects light according to its polarimetric properties. Optionally incorporated in the detector 101 is a MEMS based tunable spectral filter 102 that acts as a narrow wavelength bandpass filter. This is used where the probe laser 300 is multi-mode, and a single mode has to be selected. In front of the detector 101, but not directly incorporated on it is a tunable spectral filter, such as a liquid crystal fabry perot or acousto-optic tunable filter.

Between the probe and reference lasers, and the detector is a telescope arrangement 200 for launching the laser light towards the scene of interest; collecting the return probe and reference beams and directing them to the filter 102, 700 and the detector 100. The telescope arrangement 200 can be of any suitable design. The particular arrangement shown in FIG. 3 is the "Cassegrain" type, which is well known in the art. The telescope arrangement usually contains, as illustrated, reflective elements 201, 202, 203, but could also use transmissive elements or other optical arrangements. Telescope arrangements are well known in the art, and so will not be described herein in detail.

The probe laser 300 outputs chirped light pulses over a range of wavelengths, at least one of which is absorbed or backscattered by the target gas 600. The reference laser 400 operates at a wavelength not absorbed or backscattered by the target gas 600. Each pulse applied to both the probe and reference lasers may have a duration that is greater than 50 ns, in particular greater than 100 ns. Each applied pulse may have a duration that is in the range of 50 to 3000 ns, preferably 100 to 3000 ns. This can provide a tuning range of about 60 to 240 GHz per pulse.

Both the probe and reference laser beams 311 and 411 are launched by the telescope 200 to illuminate the background scene, the scene and/or the target. The return light reflected or backscattered by the background scene, the scene and/or the target is directed by the telescope arrangement 200 to the filter 102 and the detector 100. The detector 100 has a much slower response time than the duration of a single chirped pulse ($T_{pulse}$=1 µs for example) received from the probe 301 via the target scene. Therefore, the detector is being used as an integrator, measuring the pulse optical power amplitude by integrating the optical signal falling onto the detector area at least during a time $T_{int\ sig}$ longer that the minimum detector specified integration time ($t_{int\ det}$). In the case of QWIP for example $T_{int\ det}$ is typically in the order of 5 to 20 ms, whereas the quantum cascade lasers output pulses having durations in the range of 50 to 3000 ns, preferably 100 to 3000 ns.

The probe and reference lasers 300 and 400 may be single mode lasers. Alternatively, they may be multi-longitudinal mode lasers, but include means for causing the laser to emit in a single mode, for example a MEMS based spectral element using principle external cavity feedback (ECF) directly integrated onto the laser. In either case, the probe laser outputs a series of chirped pulses, each of which provides a wavelength scan per laser mode(s) and is operated so that the individual wavelength scans of the pulses combine to provide an extended spectrum for scanning the scene of interest.

Figure 4:
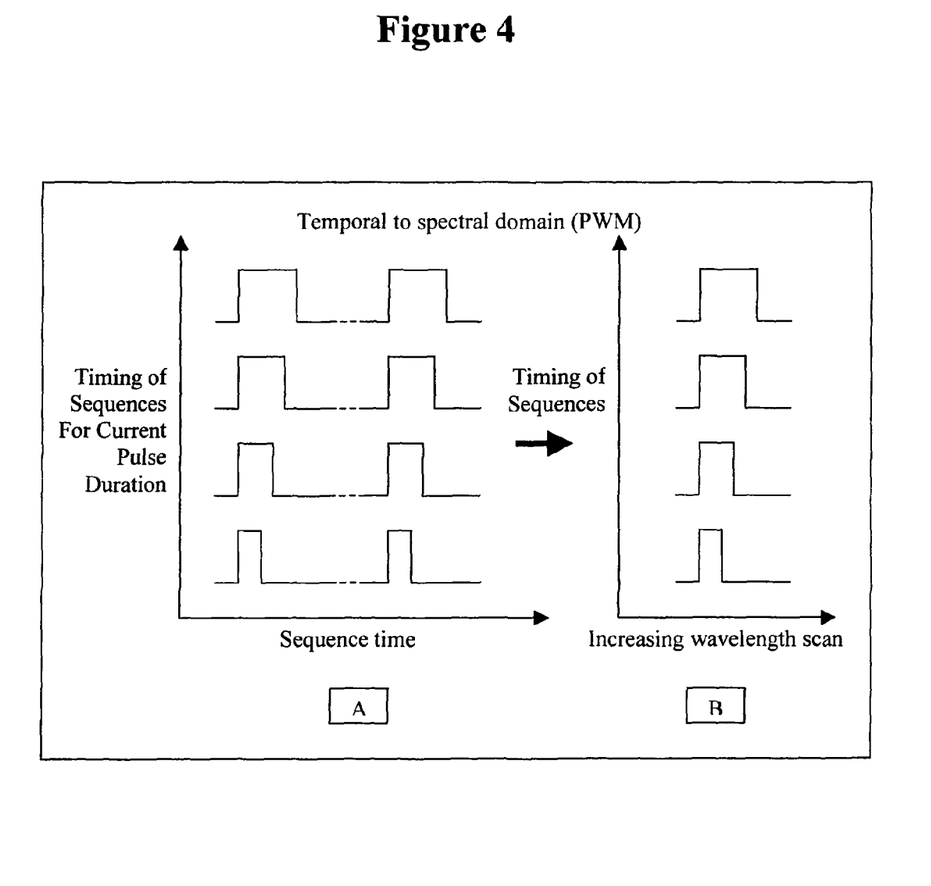
FIG. 4 shows the impact of pulse width on the wavelength chirp for single mode laser or one mode of a multi-longitudinal mode laser.

There are various techniques for varying the wavelength range of a chirped pulse thereby to provide an extended scanning range. As noted previously, the probe laser 300 is a quantum cascade laser, which has a pulsed, chirped output. By increasing or decreasing the duration of each pulse input to the laser, the relative wavelength chirp increases or decreases respectively, as shown in FIG. 4. This is described in more detail in WO03/087787, the contents of which are incorporated herein by reference. By modulating the input pulse width and combining the resultant output pulses, there is provided an extended spectrum. If the optical power is integrated and measured for at least one sequence with identical pulse duration parameters then a measurement having a specific wavelength chirp width in the spectral domain will be obtained. By then changing the duration for the following sequences whether linearly, continuously or in a coded manner a measurement having another specific wavelength chirp width can be obtained. By controlling the width, changes in the wavelength scan can be induced so that absorption spectroscopy can be carried out.

Figure 5:
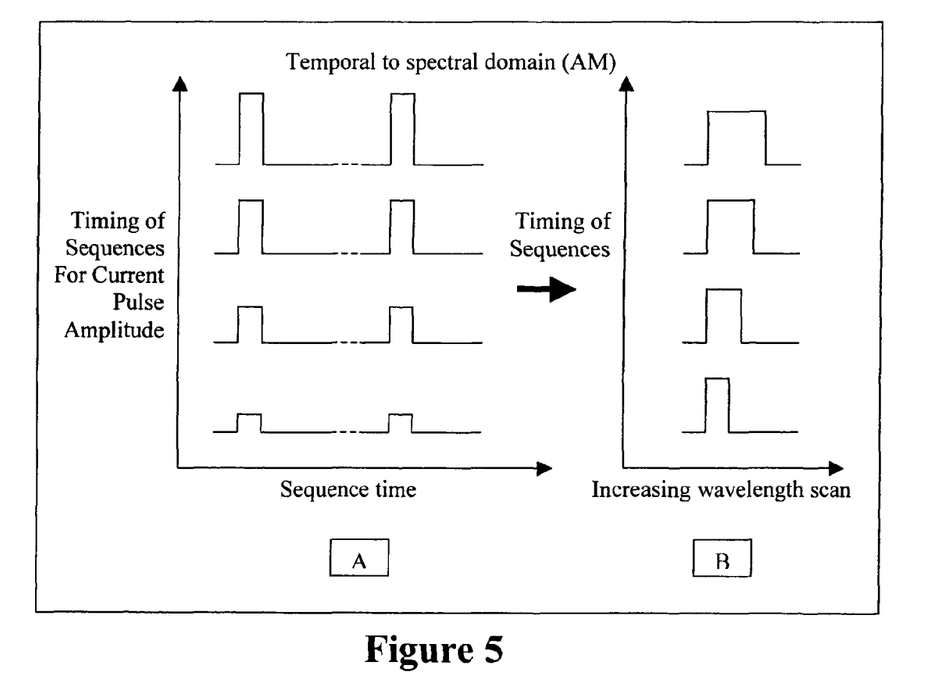
FIG. 5 shows the impact of pulse amplitude on the wavelength chirp for single mode laser or one mode of a multi-longitudinal mode laser.

Another option for varying the wavelength scan is to increase or decreases the amplitude of the laser input pulse, as described in WO03/087787. This causes the relative wavelength chirp (scan) of a semiconductor diode laser will increase or decrease respectively, as shown in FIG. 5. If the optical power is integrated and measured for at least one sequence with identical pulse current amplitude parameters a measurement having a specific wavelength chirp width in the spectral domain can be obtained. By then changing the amplitude for the following sequences whether linearly, continuously or in a coded manner a measurement having another specific wavelength chirp width can be subsequently obtained. By controlling the current pulse amplitude changes in wavelength scan can be induced, so that absorption spectroscopy can be carried out over an extended range.

Figure 6:
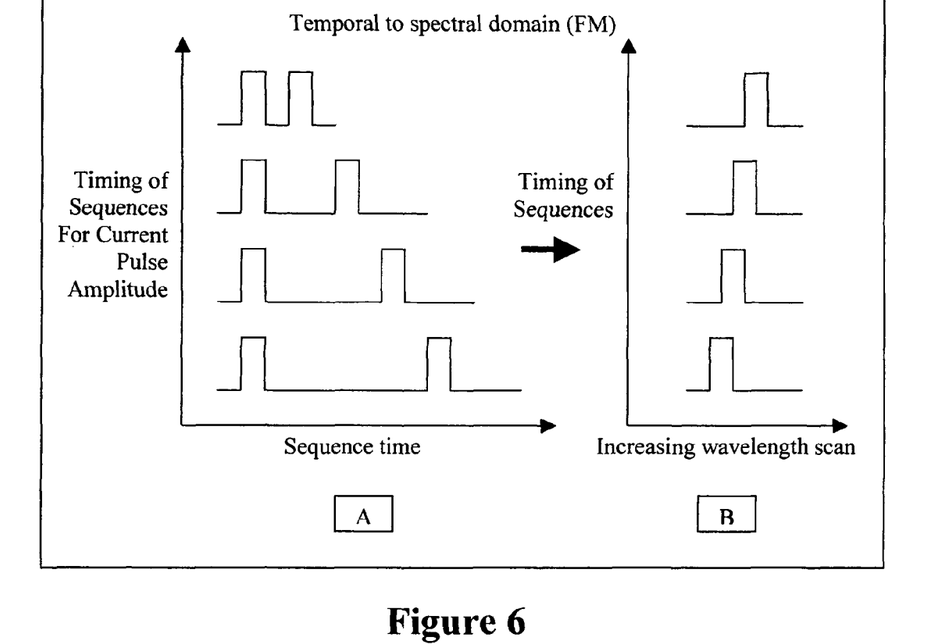
FIG. 6 shows the impact of frequency on the wavelength chirp for single mode laser or one mode of multi-longitudinal laser modes.

Yet another option for varying the wavelength scan is to increase or decrease the frequency of the input pulses, as described in as described in WO03/087787. In this case, the starting wavelength of the relative wavelength chirp (scan) will be longer or shorter respectively depending on the frequency, as shown in FIG. 6. If the optical power is integrated and measured for at least one sequence with identical pulse current amplitude, frequency and duration parameters then one will also obtain a measurement having a specific wavelength chirp width in the spectral domain. By then changing the frequency for the following sequences whether linearly, continuously or in a coded manner one will then subsequently obtain a measurement having another specific wavelength chirp width since the baseline temperature of the laser, stabilized by a peltier element of a few second time scale, will be varied much faster in a controlled manner. By controlling the laser baseline temperature one can then induced controlled changes in the start of the wavelength scan and therefore carry out absorption spectroscopy in that manner.

Figure 7:
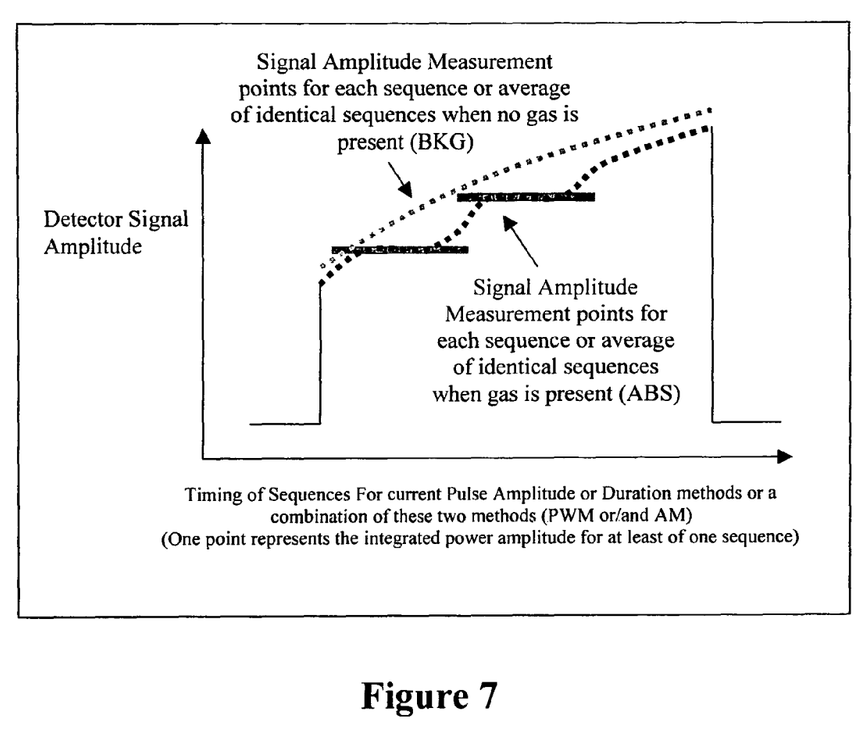
FIG. 7 shows a set of measurement points taken using a single mode laser or one mode from a multi-longitudinal mode laser, in which the pulse width and/or amplitude is varied.

FIG. 7 shows a set of measurement points, where each point represents an integrated optical power measurement for at least one sequence of current pulses having the same parameters, i.e. amplitude, duration, frequency, where the sequence duration is at least equal to $T_{int\ sig}$. Subsequent points represent an incremental linear change in the current pulse amplitude and/or width. If an absorption feature from a molecule in a gas phase is present within the wavelength chirp (scan) of a particular sequence, a change is observed from the background signal, i.e. when no gas is present. With this method the spectra can be resolved in time. This method induces a slight shift of the start wavelength of a scan or chirped with can be taken into account.

Figure 8:
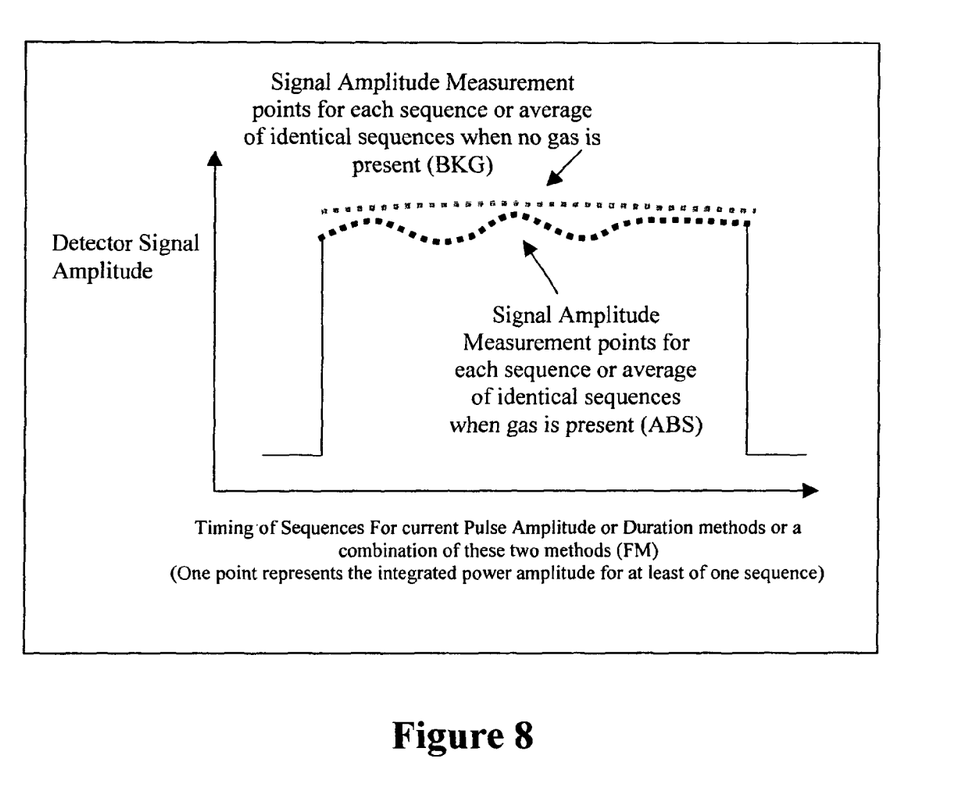
FIG. 8 shows a set of measurement points taken using a single mode laser or one mode of a multi-longitudinal mode laser, in which the pulse frequency is varied.

FIG. 8 shows measurement points, each representing an integrated optical power measurement for at least one sequence with identical current pulse parameters and where the subsequent point from the previous represent an incremental linear change in the current pulse frequency. If an absorption feature from a molecule in gas phase is present within the wavelength chirp (scan) of a particular sequence, a change from the background signal is observed.

The invention provides the possibility of very high measurement rates. For example in the narrowband or single mode operation where a gas absorption is observed at a specific wavelength, the user may choose to fix the laser settings and operate in a fixed wavelength mode of operation such system can operate at a rate of more than 100 frames per second. This enables transient effects to be measured at temporal resolutions of the order of 10 ms.

In the broadband scanning wavelength mode in which broadband emission cover the laser gain spectrum range and a tunable spectral filter or ECF system act as the wavelength selection mean selecting a narrow spectral window, it is possible to carry out a wider extended scan of for example of 100 narrow spectral window elements per second, thereby allowing the system to operate at rate more than one data cube set acquisition per second. In practice, this means that the system can be placed on a moving platform and still provide enhanced performances compared to the state of the art fixed scene systems.

The present invention has numerous applications. For example it could be used in the detection of illicit substances for drug enforcement agencies; the continuous emission monitoring from smoke stack/exhaust; leak detection in infrastructure and maintenance of infrastructure; environmental monitoring of airborne pollutants; mining and petroleum exploration and enhanced remote detection of man made objects.

A skilled person will appreciate that variations of the disclosed arrangements are possible without departing from the invention. For example, the above methods are not the only means of varying the spectral characteristics of a semiconductor diode laser source. A combination of these could be used in a linear or continuous manner, as could other modulation techniques such as Pulse Code Modulation (PCM), etc. Accordingly the above description of the specific embodiment is made by way of example only and not for the purposes of limitation. It will be clear to the skilled person that minor modifications may be made without significant changes to the operation described.

The invention claimed is:

1. A hyperspectral sensor or imager comprising a laser for illuminating a scene and a detector for detecting light emitted by the laser and transmitted through the scene, wherein the laser is a chirped laser arranged to output multiple pulses having different wavelength ranges, each chirped pulse providing a wavelength scan, and the laser being operable so that the individual wavelength scans of the chirped pulses combine to provide an extended continuous spectrum for illuminating the scene.

2. A hyperspectral sensor or imager as claimed in claim 1 wherein the multiple pulses combining to form an extended continuous spectrum for illuminating the scene have wavelengths ranging from 1 µm to 20 µm.

3. A hyperspectral sensor or imager as claimed in claim 1 comprising a polarization sensitive filter adapted to allow light from the laser to pass but substantially block background radiation.

4. A hyperspectral sensor or imager as claimed in claim 1 wherein the detector is polarization sensitive and adapted to allow light from the laser to pass but substantially block background radiation.

5. A hyperspectral sensor or imager as claimed in claim 1 wherein the detector is a two dimensional focal plane detector.

6. A hyperspectral sensor or imager as claimed in claim 1 wherein the detector is a QWIP.

7. A hyperspectral sensor or imager as claimed in claim 1 wherein the detector is one of: a MCT detector; a selenide based detector; a superlattice type II detector.

8. A hyperspectral sensor or imager as claimed in claim 1 wherein the detector is operable to detect only polarized light generated by the chirped laser.

9. A hyperspectral sensor or imager as claimed claim 1 wherein the laser is a semiconductor laser.

10. A hyperspectral sensor or imager as claimed in claim 1 wherein the laser is a quantum cascade laser.

11. A hyperspectral sensor or imager as claimed in claim 9 comprising means for applying to the laser pulses that have a duration that is greater than 50 ns.

12. A hyperspectral sensor or imager as claimed in claim 11 wherein each applied pulse has a duration that is in the range of 50 to 3000 ns.

13. A hyperspectral sensor or imager as claimed in claim 1 wherein the different laser output pulses are generated by varying one or more of the following features of the pulse applied to the laser; pulse width; pulse-amplitude; pulse frequency.

14. A hyperspectral sensor or imager as claimed in claim 1 comprising a solid state tunable spectral filter.

15. A hyperspectral sensor or imager as claimed in claim 14 wherein the filter is a liquid crystal fabry perot (LCFP) or acousto-optic tunable filter (AOTF).

16. A hyperspectral sensor or imager as claimed in claim 14 wherein the filter is placed between the laser and the detector.

17. A hyperspectral sensor or imager as claimed in claim 1 comprising a tunable filter directly integrated onto the detector.

18. A hyperspectral sensor or imager as claimed in claim 17 wherein the tunable filter is a micro-electro-mechanical system (MEMS).

19. A hyperspectral sensor or imager as claimed in claim 1 wherein the laser is a single mode laser.

20. A hyperspectral sensor or imager as claimed in claim 1 wherein the laser is a multi-mode longitudinal laser.

21. A hyperspectral sensor or imager as claimed in claim 20 comprising a tunable spectral filter for scanning through the multiple modes.

22. A hyperspectral sensor or imager as claimed in claim 21 wherein the spectral filter is a solid state tunable spectral filter.

23. A hyperspectral sensor or imager as claimed in claim 20 comprising means for causing the multi-mode longitudinal laser to operate in a single mode.

24. A hyperspectral sensor or imager as claimed in claim 23 wherein the means for causing the multi-mode longitudinal laser to operate in a single mode comprise a micro-electro-mechanical system (MEMS) based spectral element.

25. A hyperspectral sensor or imager as claimed in claim 24 wherein the MEMS element uses external cavity feedback (ECF).

26. A hyperspectral sensor or imager as claimed in claim 24 wherein the MEMS element is directly integrated onto the laser.

27. A hyperspectral sensor or imager as claimed in claim 1 wherein the multiple pulses combining to form an extended continuous spectrum for illuminating the scene have wavelengths ranging from 7 μm to 14 μm.

28. A hyperspectral sensor or imager as claimed in claim 11 wherein each applied pulse has a duration that is in the range of 100 to 3000 ns.

29. A hyperspectral sensor or imager as claimed in claim 9 comprising means for applying to the laser pulses that have a duration that is greater than 100 ns.

* * * * *